United States Patent [19]
Poissant

[11] Patent Number: 5,569,843
[45] Date of Patent: Oct. 29, 1996

[54] UNIT USED IN AN APPARATUS FOR MEASURING THE VISCOSITY OF A FLUID

[75] Inventor: Daniel Poissant, St-Hubert, Canada

[73] Assignee: PAD Peripheral Advanced Design, Inc., Canada

[21] Appl. No.: 419,818

[22] Filed: Apr. 11, 1995

[51] Int. Cl.[6] .................................................. G01N 11/06
[52] U.S. Cl. ........................................ 73/54.07; 73/54.13
[58] Field of Search ............................... 73/54.01, 54.04,
73/54.07, 54.13, 54.36, 863.71, 863.73,
864.13, 864.16

[56] References Cited

U.S. PATENT DOCUMENTS

| | | | |
|---|---|---|---|
| 4,388,823 | 6/1983 | Garnaud et al. | 73/54.18 |
| 4,517,830 | 5/1985 | Gunn | 73/54.17 |
| 4,868,849 | 9/1989 | Wright | 73/54.31 |
| 5,327,778 | 7/1994 | Park | 73/54.21 |
| 5,388,447 | 2/1995 | Fitch et al. | 73/54.14 |

*Primary Examiner*—Richard Chilcot
*Assistant Examiner*—Max H. Noori
*Attorney, Agent, or Firm*—Merchant, Gould, Smith, Edell, Welter & Schmidt

[57] ABSTRACT

The disclosure herein describes a unit used in an apparatus for measuring the viscosity of a fluid contained in a recipient; the unit includes a vertically displaceable piston at the upper end of which is provided a lifting plate while the lower end is equipped with a spherical head displaceably received in a cup immerged in the fluid. As the piston is lifted, fluid is drawn into the cup. After being raised, the piston is allowed to fall under gravity and the fluid in the cup is expelled through a small clearance between the spherical head and the inner cylindrical wall of the cup. The time required for the piston plate to contact and actuate a switch is proportional to the viscosity of the fluid.

10 Claims, 3 Drawing Sheets

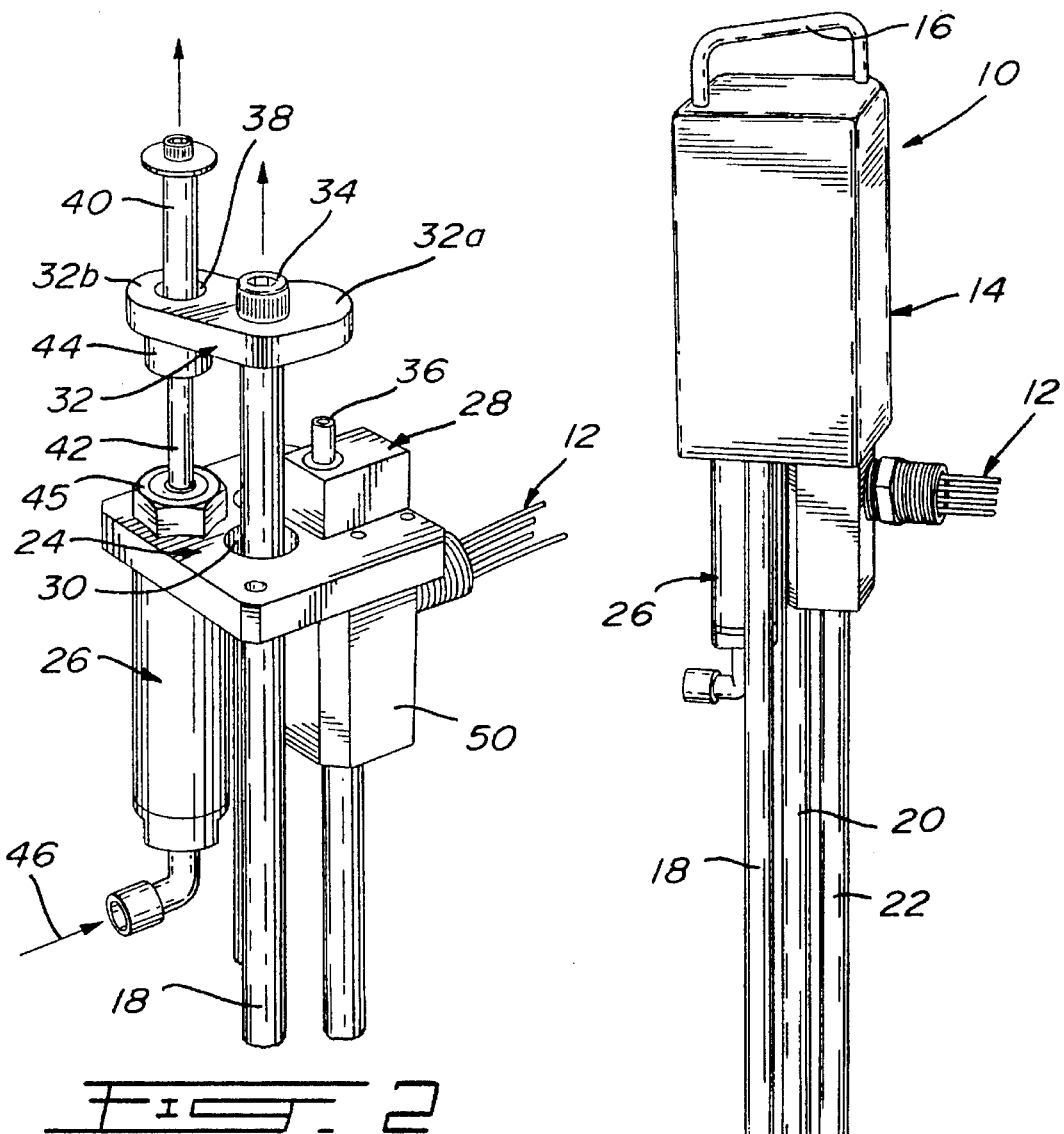
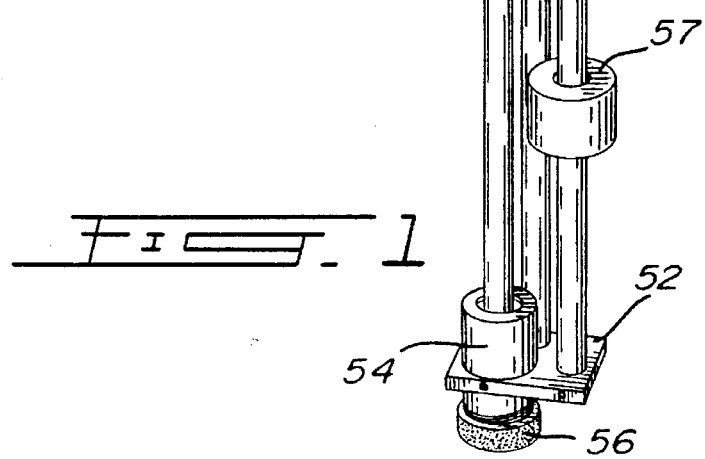

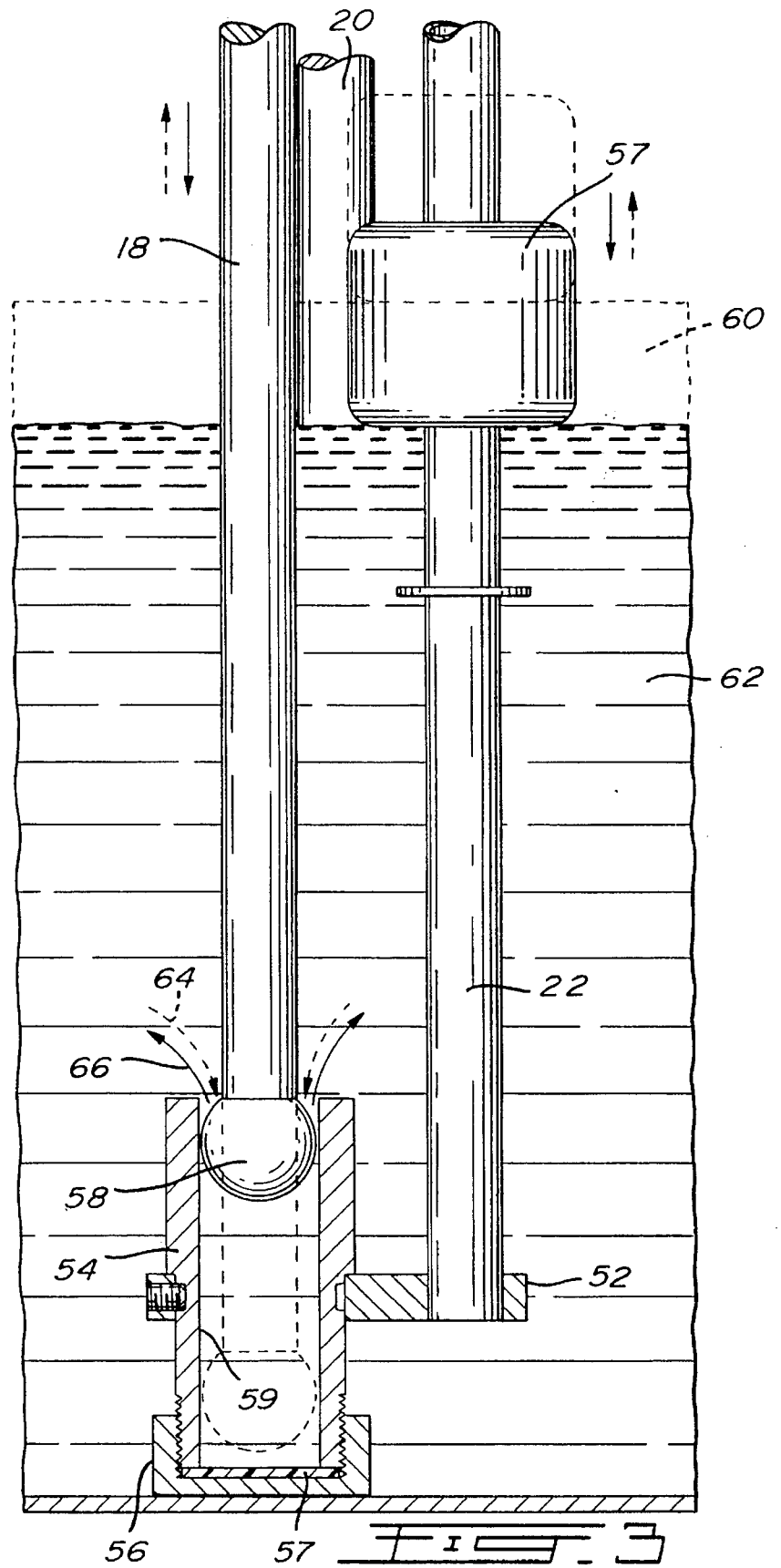

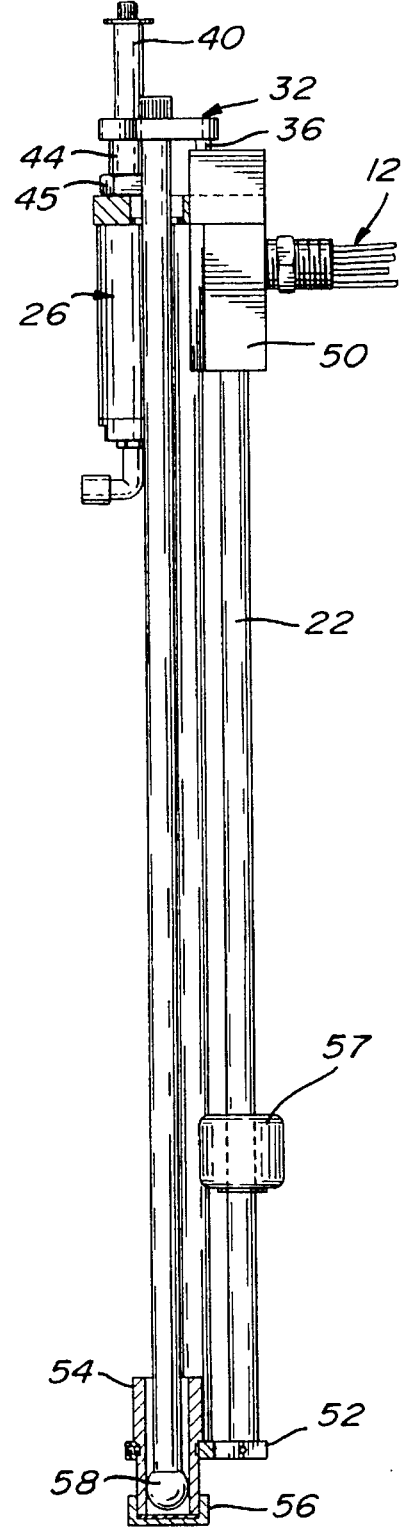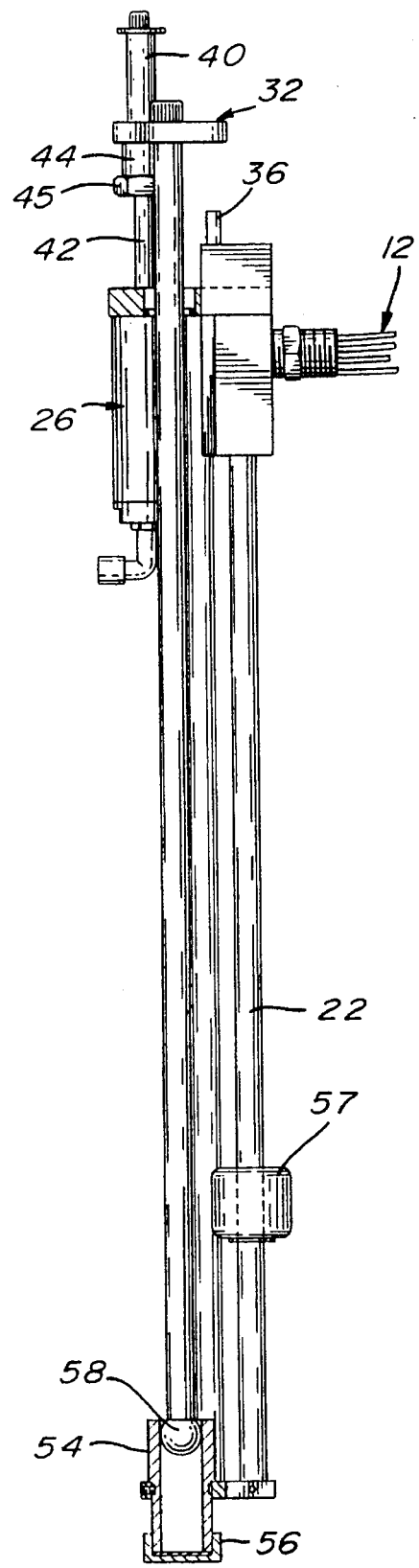

5,569,843

UNIT USED IN AN APPARATUS FOR MEASURING THE VISCOSITY OF A FLUID

FIELD OF THE INVENTION

The present invention pertains to an improvement in a unit associated with an apparatus that is used for measuring the viscosity of a fluid contained in a recipient.

BACKGROUND OF THE INVENTION

The operation of such apparatus is based on the Archimedes principle. A measuring element is immersed in the fluid to be measured. When an actuating mechanism is operated, the measuring element is raised to a given height. During its ascension, a vacuum is created in the cavity of a cup in which the lower end of the measuring element is contained. The measuring element is maintained in the raised position during an adequate period of time so as to ensure that the cup cavity is completely filled. When the actuating mechanism is released, the measuring element falls under gravity and, after having travelled a given distance, a detector is actuated to detect the end of the cycle. The time elapsed is proportional to the viscosity of the fluid.

Current systems utilize a piston which has a cylinder at its lower end that is displaced in a cylindrical cup; such systems have two major drawbacks. First, often, during their operation, the measuring units are subjected to heavy mechanical shocks (for example, they may accidently be dropped on a cement floor). If one considers that a distance of at least 0.007 inch usually separates the measuring cylinder from the cylindrical cup wall within which it is housed, any minor misalignment between these two parts will greatly affect measurement readings. This device is therefore extremely vulnerable.

A second problem, more technical, concerns fluid mechanics. If one desires to have a fluid to circulate with a given flow through a gap having a constant diameter and a given length, a certain pressure must be applied to evacuate the fluid. If the length of this gap is increased, while maintaining the same flow, the pressure must be increased. Therefore, by using a piston with a cylindrical head, the length of the gap will increase as the piston descends into the cylinder. Since the pressure is constant (weight of the cylinder and constant gravity pull), the fluid will have increasing difficulty escaping through the gap. This will result in a reduction of speed which is exponential as the piston descends. It has been noted that, at very low speed, this concept becomes inaccurate and unstable, which therefore results in the extremely important need to maintain a constant speed during the entire measuring process.

OBJECTS AND STATEMENT OF THE INVENTION

An object of the present invention is to overcome the above problems pertaining to present fluid measuring apparatus using the combination of a cylinder into a cylindrical cup.

This is achieved by replacing the lower end of the piston by a spherical head. The use of a spherical head eliminates the problem of misalignment since it is based on the concept of a rotulus.

Furthermore, by using the spherical head concept, the length of the gap is constant during the entire descent. By using a sphere, the length of the gap is equal to the tangent at the point of contact between the spherical head and the hollow cylinder. This distance is very small and constant during the entire displacement. The speed of descent of the measuring head will therefore be constant throughout its travel.

The present invention therefore relates to an improvement in an apparatus for measuring the viscosity of a fluid contained within a recipient; it comprises a unit that includes:

vertically displaceable piston means having an upper part and a lower part, the upper part including a switch contacting means; the lower part being immergedly receivable within the fluid containing recipient and displaying a spherical head at a lower end thereof;

cup means receiving the spherical head therein and displaying an inner cylindrical wall having an inner diameter slightly greater than the diameter of the spherical head to thereby provide a linear clearance between the head and the cup wall;

means associated with the upper part of the piston means for lifting the piston means to an uppermost position and for allowing, at this position, the piston means to fall under gravity to a lower switch contacting position whereby the time for the piston means to reach the lower position, as the fluid is expelled through the clearance from the cup means, is proportional to the viscosity of the fluid.

In one form of the invention, a combination of a lifting plate and of a lifter associated with a pneumatic piston allows for a time delay to enable the fluid to completely fill the cup means under the spherical head.

Other objects and further scope of applicability of the present invention will become apparent from the detailed description given hereinafter. It should be understood, however, that this detailed description, while indicating preferred embodiments of the invention, is given by way of illustration only, since various changes and modifications within the spirit and scope of the invention will become apparent to those skilled in the art.

BRIEF DESCRIPTION OF THE DRAWINGS

FIG. 1 is a perspective view of a unit made in accordance with the present invention;

FIG. 2 is a perspective view of the upper part of the unit with its housing removed;

FIG. 3 is an enlarged elevation view, partly cross sectional, showing the lower part of the unit immerged in a fluid containing recipient;

FIG. 4 is a side view, partly cross sectional, showing the unit in the uppermost lifted position; and FIG. 5 is a view similar to FIG. 4 showing the piston means in the lowermost switch contacting position.

DESCRIPTION OF PREFERRED EMBODIMENTS

Referring to FIG. 1, there is shown a unit, generally denoted 10, which forms part of an apparatus for measuring the viscosity of a fluid contained within a recipient. This unit shows a series of electrical conductors 12 which serve to forward electrical signals measured by the unit to an information gathering and displaying device (not shown) which is standard and forms part of the apparatus.

The unit 10 comprises a housing 14, the top wall of which is provided with a handle 16 allowing it to be carried while, from the underface of which extend three parallel vertical rods 18, 20 and 22, the function of each which will be described further hereinbelow.

Referring also to FIG. 2, enclosed in the housing 14 is a top plate 24 to which it is fixedly secured by appropriate fastening means not shown. This top plate 24 supports a pneumatic cylinder 26 and is fixed thereto by means of a bolt 45. A switch device 28 is also supported by the top plate 24. The latter displays a circular opening 30 through which extends the vertical rod 18. The upper end of rod 18 is fixedly secured to a lifting plate or arm 32 by means of a bolt 34. One side 32*a* of the lifting plate extends over a resiliently biased actuator 36 of the switch device 28 while the opposite side 32*b* of the plate is provided with an opening 38 through which extends the upper extension 40 of a lifter rod fixed to the upper end of the piston 42 of the pneumatic cylinder 26. The lifter rod has an enlarged lower portion 44 which contacts the undersurface 25 of the lifting plate portion 32*b*. Air pressure supplied to the cylinder 26 (as indicated by arrow 46) causes the piston 42 to be raised as well as the lifter rod 40 and, through the contact engagement of its enlarged lower part 44, the lifting plate 32 is also raised.

The switch device 28 has a lower housing 50 extending below plate 24 and serves to enclose electrical contacts and associated circuitry to transmit signals, via wires 12, to the information gathering and displaying device of the measuring apparatus.

Referring to FIGS. 1 and 3, the lower part of the unit 10 comprises a lower plate 52 to which is secured the lower end of rod 20; this lower plate forms a structural frame with the top plate 24 and the rod 20. A cup shaped member is fixedly secured to plate 52 and consists of a cylindrical hollow member 54, the bottom of which is threadedly and sealingly closed by a cap 56 and seal 57.

The present invention is particularly concerned with the mounting of a spherical head 58 to the lower end of rod 18. The diameter of the inner wall 59 of the hollow cylinder 54 is slightly greater than the outer diameter of the spherical head so as to leave a small clearance (about 0.007 inch).

Also received in plate 52 and extending from the upper housing 50 is the third rod 22 on which is mounted a float member 57 which does not form part of the present invention, but which may be used to provide fluid level indication to the information gathering and displaying device via the electrical connectors 12.

A description of the operation of the present unit will now be given with respect to FIGS. 3, 4 and 5.

In a recipient 60, a fluid 62 is contained in order to obtain a measurement of its viscosity. As described above, the actuation of the pneumatic device 26 causes the lifter arm 32 to be raised thereby lifting the spherical head 58 from the dotted to the full lines shown in FIG. 3. This lifting motion causes a vacuum below the spherical head drawing fluid into the cup 54 as indicated by arrows 64.

By cutting off air pressure to the cylinder 26, the piston rod 42 and the lifter 40 move downwardly until the enlarged portion 44 of the lifter contacts bolt 45 on the top plate 24. By having the lifter 40 extending beyond the top face of the lifter arm 32, the sudden downward motion of the piston rod 42 does not cause an immediate downward rapid descent of the lifter arm 32. This enables time for the cup to be filled with fluid under the spherical head while allowing the piston means to freely fall under the effect of gravity. The downward speed of movement of plate 32 and of piston 18 with its spherical lower head 58 depends on the viscosity of the fluid 62 so that, as the spherical head is lowered into the cylinder 54, there is an outward flow of the fluid (as indicated by arrows 66) passing by the clearance between the head and the cylinder. Hence, the amount of time that the lifter arm 32 takes to move from its uppermost position, as illustrated in FIG. 4, to reach its lowermost position, as illustrated in FIG. 5, is 10 proportional to the viscosity of the fluid in the recipient 60. Therefore, the time of fall by gravity is a measure of viscosity. The clearance between the piston head and the inner wall of the cylinder form the measuring gap.

Although the invention has been described above with respect with one specific form, it will be evident to a person skilled in the art that it may be modified and refined in various ways. It is therefore wished to have it understood that the present invention should not be limited in scope, except by the terms of the following claims.

The embodiments of the invention in which an exclusive property or privilege is claimed are defined as follows:

1. In an apparatus for measuring the viscosity of a fluid contained within a recipient, the improvement comprising a unit including:

vertically displaceable piston means having an upper part and a lower part; said upper part including a switch contacting means; said lower part being immergedly receivable within the fluid containing recipient and displaying a spherical head at a lower end thereof;

cup means receiving said spherical head therein and displaying an inner cylindrical wall having an inner diameter slightly greater than the diameter of the spherical head to thereby provide a linear clearance between said head and said wall;

means associated with the upper part of said piston means for lifting said piston means to an uppermost position and for allowing, at said uppermost position, said piston means to fall under gravity to a lower switch contacting position whereby the time for said piston means to reach said lower position, as said fluid is expelled through the clearance from the cup means, is proportional to the viscosity of the fluid.

2. In an apparatus as defined in claim 1, said unit including a frame consisting of an elongated vertically extending member, of a top plate at an upper end of said member and of a bottom plate at a lower end thereof.

3. In an apparatus as defined in claim 2, said unit including switch means mounted to said top plate.

4. In an apparatus as defined in claim 3, wherein said piston means consist of an elongated vertical rod and of a lifting plate fixedly secured to the upper end of said rod; said lifting plate having a first portion contacting said switch means after said piston means falls under gravity.

5. In an apparatus as defined in claim 4, wherein said associated means include a pneumatic actuator including a piston and a rod, said actuator rod contacting a second portion of said lifting plate to raise said piston means to said uppermost position.

6. In an apparatus as defined in claim 5, wherein said second portion of said lifting plate includes an opening therethrough; said actuator piston having, at the upper end thereof, a lifter having a first portion extending through said opening and a second portion to contacting the undersurface of said lifting plate to raise said lifting plate upon actuation of said associated means.

7. In an apparatus as defined in claim 2, wherein said cup means is fixedly mounted to said bottom plate of said piston means.

8. In an apparatus as defined in claim 7, wherein said cup means consist of a hollow cylinder and of a lid threadedly and sealingly engaged to the lower end of said cylinder.

9. In an apparatus as defined in claim 4, said unit including a housing fixedly secured to said top plate and enclosing therein said switch means and said lifting plate.

10. In an apparatus as defined in claim 9, wherein said housing has a top wall equipped with a handle thereon allowing said unit to be carried.

* * * * *